(12) United States Patent
Lloyd et al.

(10) Patent No.: US 12,090,711 B2
(45) Date of Patent: Sep. 17, 2024

(54) CONTROLLING A FLUID FLOW

(71) Applicant: ILC Dover LP, Frederica, DE (US)

(72) Inventors: Hayden Lloyd, Millsboro, DE (US);
Kraig Ford, Dover, DE (US); Perry Lee Millman, Greenwood, DE (US);
Mark John Brown, Jr., Wilmington, DE (US)

(73) Assignee: ILC Dover LP, Frederica, DE (US)

( * ) Notice: Subject to any disclaimer, the term of this patent is extended or adjusted under 35 U.S.C. 154(b) by 0 days.

(21) Appl. No.: 17/818,480

(22) Filed: Aug. 9, 2022

(65) Prior Publication Data
US 2023/0040059 A1    Feb. 9, 2023

Related U.S. Application Data

(60) Provisional application No. 63/231,125, filed on Aug. 9, 2021.

(51) Int. Cl.
*B29C 65/00* (2006.01)
*A61J 1/14* (2023.01)
(Continued)

(52) U.S. Cl.
CPC ......... *B29C 66/8511* (2013.01); *A61J 1/1487* (2015.05); *A61M 39/10* (2013.01);
(Continued)

(58) Field of Classification Search
CPC .... A61M 39/10; A61M 5/1414; A61M 39/12; A61J 1/10; B65D 2575/583;
(Continued)

(56) References Cited

U.S. PATENT DOCUMENTS 4,732,299 A * 3/1988 Hoyt ................... B29C 66/1122
                                                    383/906
4,998,990 A * 3/1991 Richter ................ B65D 77/065
                                                    493/929
(Continued)

FOREIGN PATENT DOCUMENTS

CN       202207305       5/2012
EP        2218433        8/2010
(Continued)

OTHER PUBLICATIONS

International Search Report and Written Opinion in International Appln. No. PCT/US2022/039823, mailed on Nov. 17, 2022, 15 pages.

*Primary Examiner* — Adam Marcetich
(74) *Attorney, Agent, or Firm* — Fish & Richardson P.C.

(57) ABSTRACT

A biopharmaceutical flow port, a biopharmaceutical liquid container assembly, and a method for manufacturing the biopharmaceutical flow port and the biopharmaceutical liquid container assembly are described. The biopharmaceutical flow port includes a hose barb coupled to an elliptic body. The hose barb includes a bore. The elliptic body includes a flow passage, a first edge, and a second edge. The flow passage is fluidly coupled to the bore. The first edge extends from the elliptic body away from the flow passage in a first direction and the second edge extends from the elliptic body away from the flow passage in a second direction opposite the first direction. The biopharmaceutical liquid container assembly includes a biopharmaceutical liquid container with an opening and the biopharmaceutical flow port coupled to the biopharmaceutical liquid container within the opening and in fluid communication with a volume of the biopharmaceutical liquid container.

23 Claims, 15 Drawing Sheets

SECTION A-A

(51) Int. Cl.
*A61M 39/10* (2006.01)
*B29C 65/02* (2006.01)
*F16L 33/035* (2006.01)

(52) U.S. Cl.
CPC .............. *B29C 65/02* (2013.01); *B29C 66/43* (2013.01); *F16L 33/035* (2013.01)

(58) Field of Classification Search
CPC .. B65D 75/5883; B65D 75/008; B65D 31/14; B65D 31/142; B65D 31/145; B65D 77/10; B65D 77/12; B65D 2575/58
See application file for complete search history.

(56) References Cited

U.S. PATENT DOCUMENTS

| | | | |
|---|---|---|---|
| 5,498,253 A * | 3/1996 | Aswad | A61J 1/10 604/905 |
| 6,241,122 B1 * | 6/2001 | Araki | B65D 51/223 222/464.2 |
| 6,273,307 B1 * | 8/2001 | Gross | B65D 75/5883 220/613 |
| 6,302,300 B1 * | 10/2001 | Bosch | B29D 23/20 222/107 |
| 6,439,429 B1 * | 8/2002 | Gross | B65D 75/5883 222/153.02 |
| 2004/0155045 A1 * | 8/2004 | Wild | B65D 75/008 220/703 |
| 2004/0238564 A1 * | 12/2004 | Bourque | B65D 75/5883 222/92 |
| 2005/0040181 A1 * | 2/2005 | Kurosawa | B65D 75/5883 222/92 |
| 2005/0173455 A1 * | 8/2005 | Hagihara | B65D 75/5883 222/107 |
| 2006/0052738 A1 * | 3/2006 | Ramella | A61M 1/1666 604/19 |
| 2007/0027437 A1 * | 2/2007 | Burg | A61J 1/10 604/415 |
| 2008/0009783 A1 * | 1/2008 | Branderburger | A61M 39/20 604/30 |
| 2008/0173614 A1 * | 7/2008 | Matsuoka | B65D 1/0223 215/384 |
| 2008/0210715 A1 * | 9/2008 | Tanaka | B65D 47/32 222/479 |
| 2009/0060398 A1 * | 3/2009 | Kawakami | B65D 75/5822 383/93 |
| 2009/0220176 A1 * | 9/2009 | Fusco | B65D 31/14 383/44 |
| 2009/0261154 A1 * | 10/2009 | Scheu | B31B 50/84 229/218 |
| 2009/0326481 A1 * | 12/2009 | Swisher | A61M 39/10 604/537 |
| 2010/0038386 A1 * | 2/2010 | Pritchard | B65D 75/008 222/530 |
| 2010/0065588 A1 * | 3/2010 | Brannon | B65D 47/06 222/564 |
| 2011/0007987 A1 * | 1/2011 | Davideit | B65D 83/425 383/42 |
| 2011/0127277 A1 * | 6/2011 | Nikitine | B65D 1/40 220/669 |
| 2011/0210092 A1 * | 9/2011 | Meager | B65D 5/746 220/694 |
| 2011/0266796 A1 | 11/2011 | Monroe et al. | |
| 2012/0284991 A1 | 11/2012 | Kusz et al. | |
| 2013/0202228 A1 * | 8/2013 | Murray | B65D 33/16 383/42 |
| 2013/0334161 A1 * | 12/2013 | Meager | B65D 47/32 215/386 |
| 2014/0175126 A1 * | 6/2014 | Carlsson | A61M 39/10 222/145.5 |
| 2014/0376834 A1 * | 12/2014 | Callahan | B65D 75/52 383/119 |
| 2016/0200494 A1 | 7/2016 | Harada et al. | |
| 2017/0096273 A1 * | 4/2017 | Mazurkiewicz | B65D 75/5883 |
| 2018/0021218 A1 * | 1/2018 | Brosch | A61J 1/10 428/35.2 |
| 2018/0111725 A1 * | 4/2018 | Gerbaulet | B65D 47/2031 |
| 2018/0201415 A1 * | 7/2018 | Berge | B65D 41/3428 |
| 2019/0084742 A1 * | 3/2019 | Schoonderbeek | F01N 3/2896 |
| 2019/0119024 A1 * | 4/2019 | Tamarindo | B65B 39/004 |
| 2019/0161230 A1 * | 5/2019 | Katsuta | B65D 1/0223 |
| 2020/0071023 A1 * | 3/2020 | Nyuu | B65D 35/14 |

FOREIGN PATENT DOCUMENTS

| | | | | |
|---|---|---|---|---|
| EP | 2253298 A1 * | 11/2010 | ............ | A61J 1/1475 |
| FR | 3096875 A1 * | 12/2020 | ............ | A45D 34/02 |
| JP | H05201441 A * | 8/1993 | ............ | B65D 47/06 |
| JP | 2000103441 A * | 4/2000 | | |
| JP | 2007320626 A * | 12/2007 | | |
| WO | WO 2010/029853 | 2/2012 | | |
| WO | WO-2021053237 A1 * | 3/2021 | ............ | A61J 1/1487 |

* cited by examiner

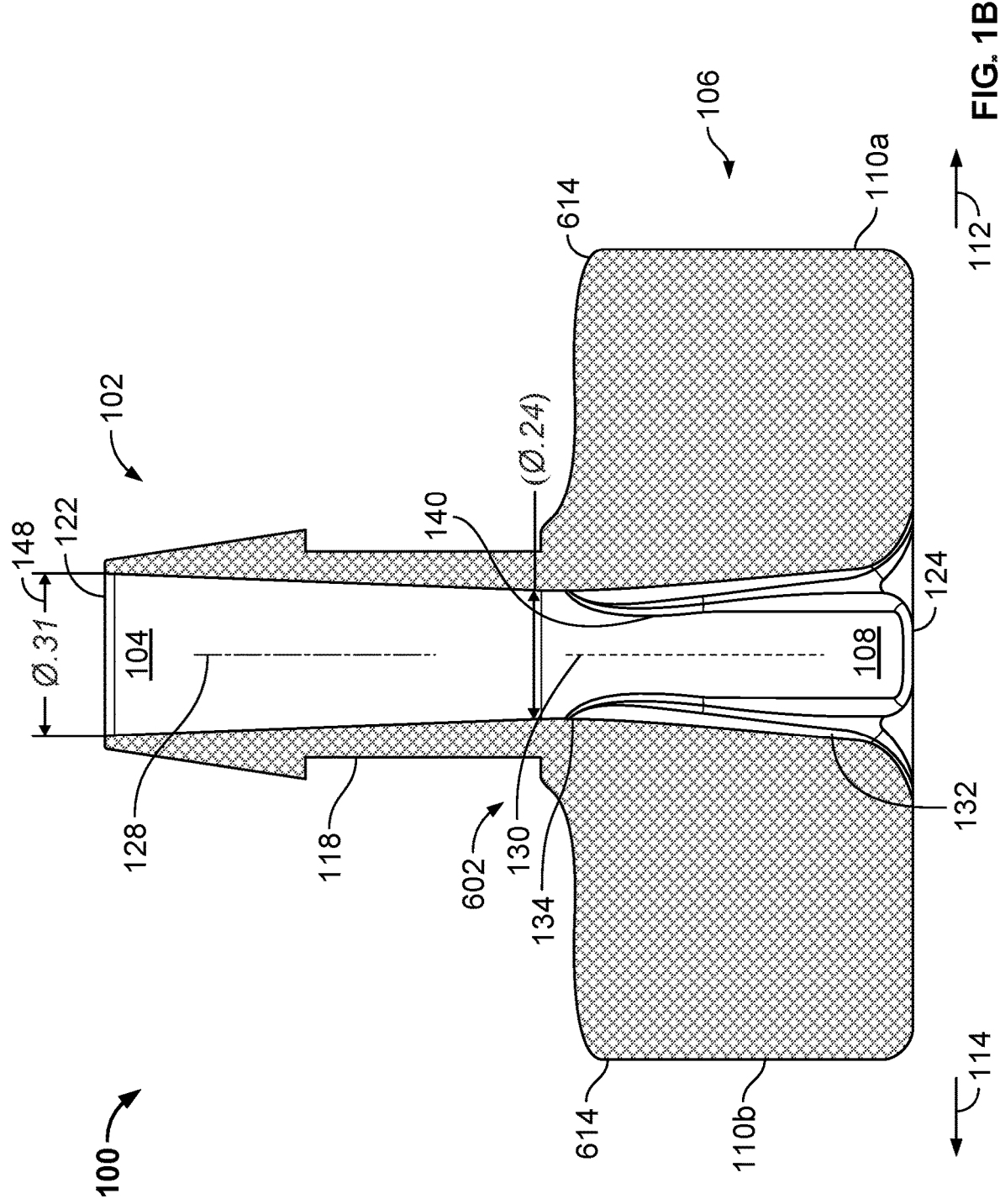

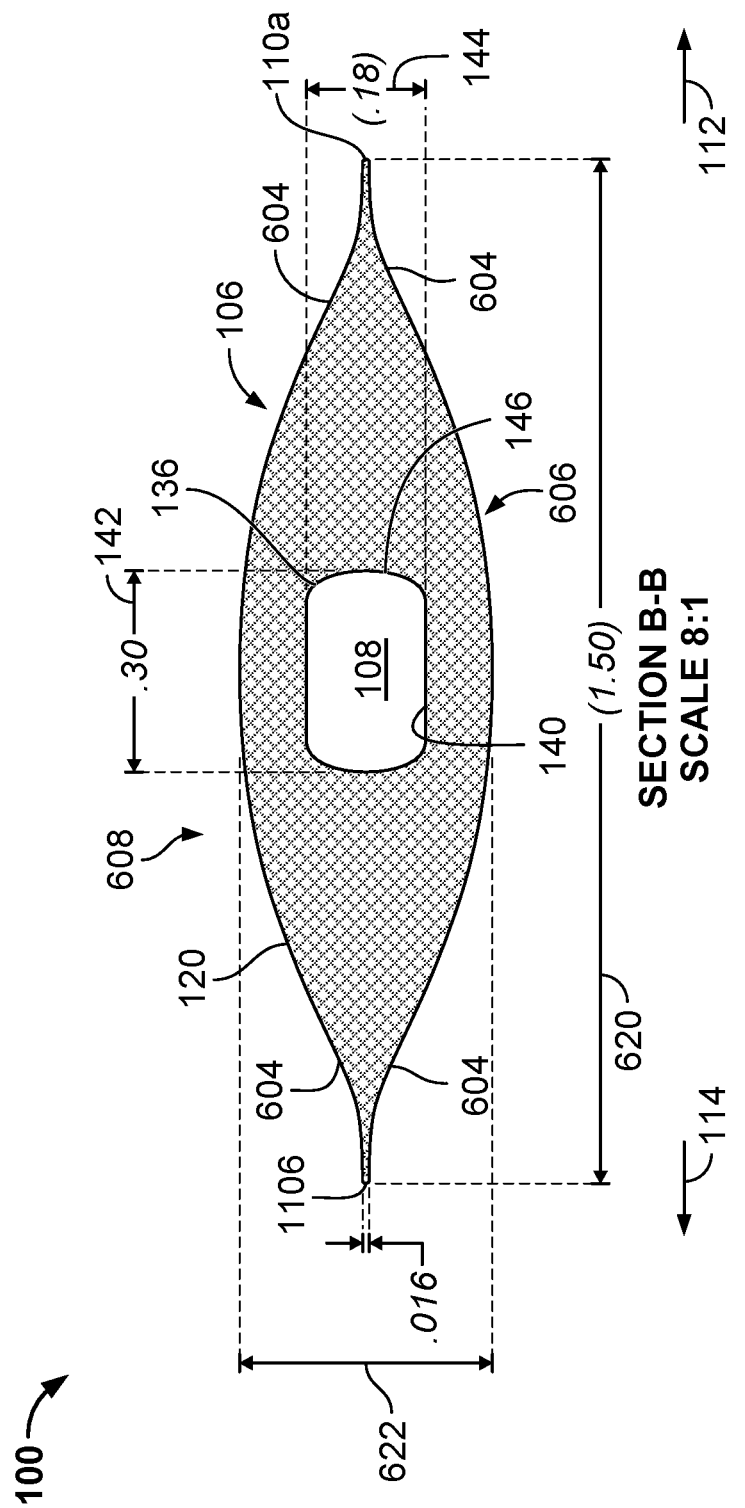

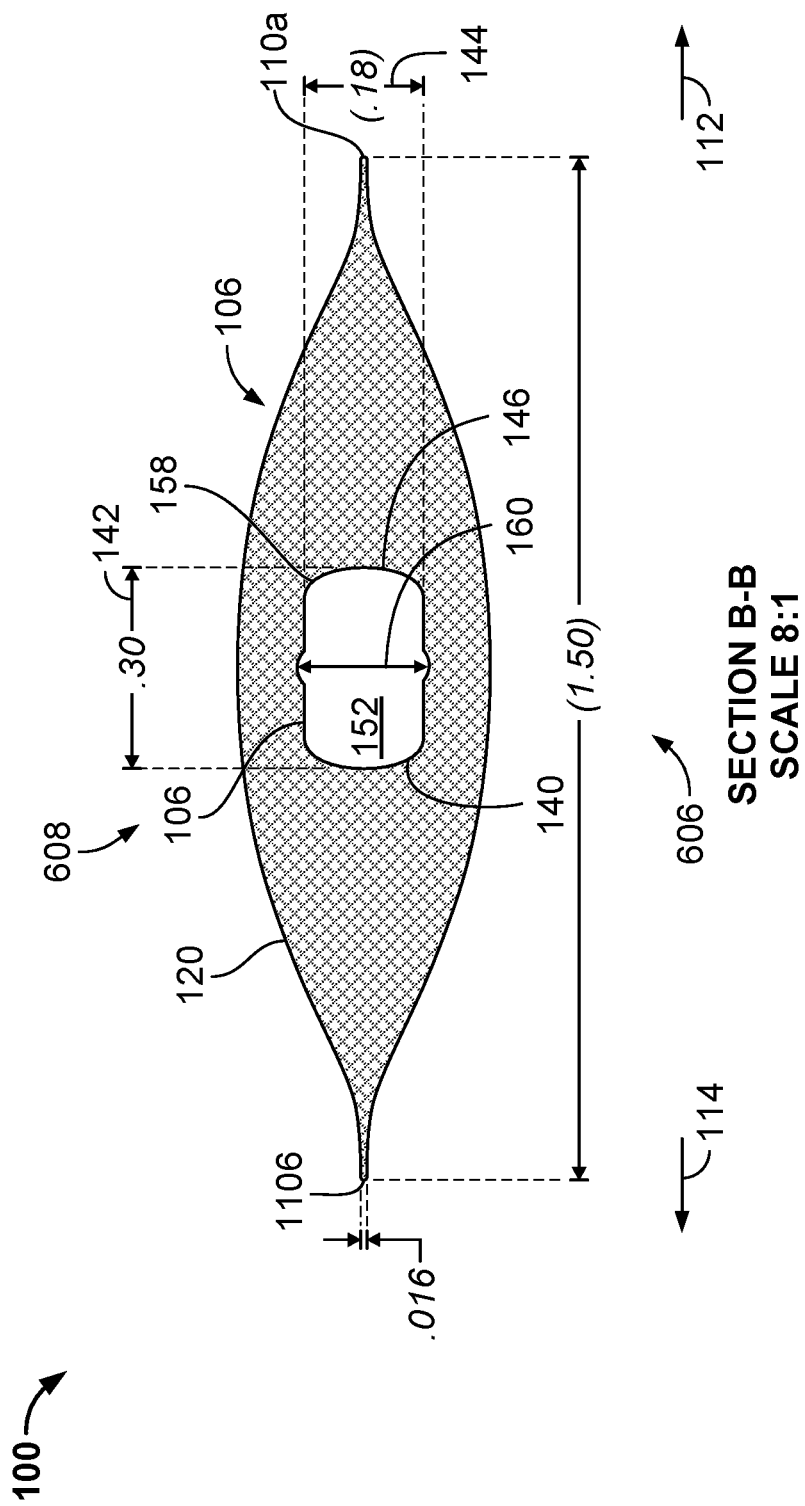

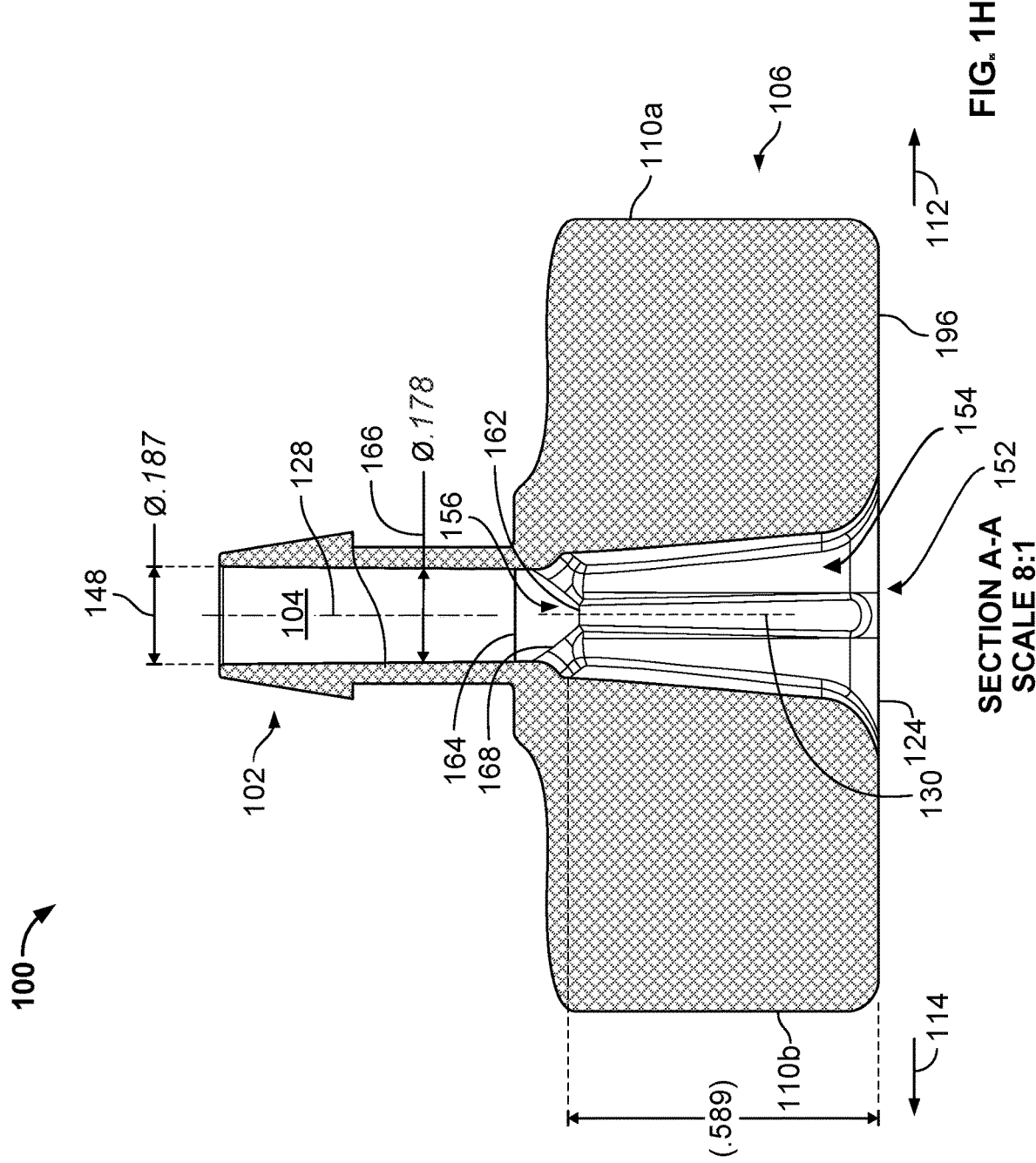

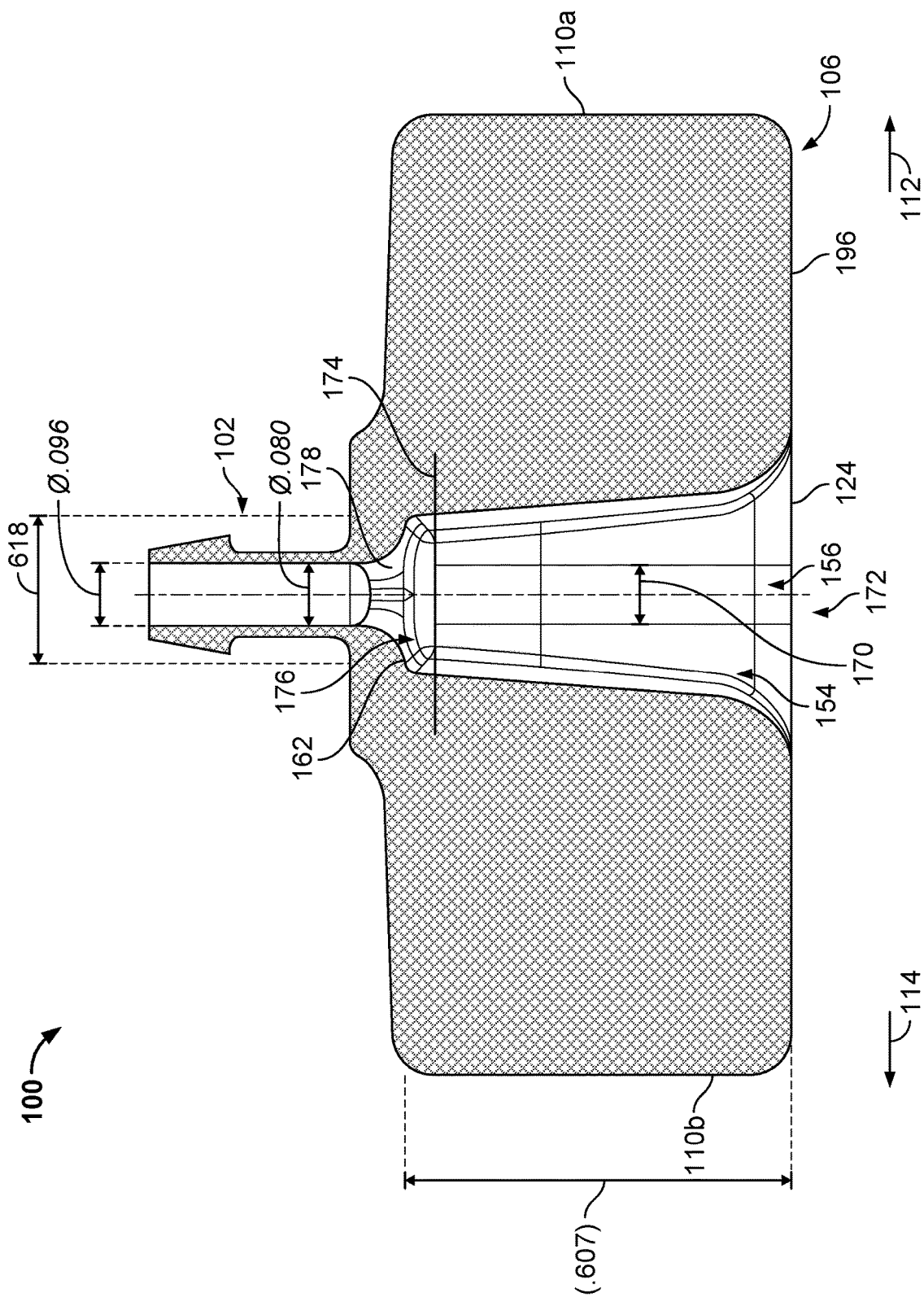

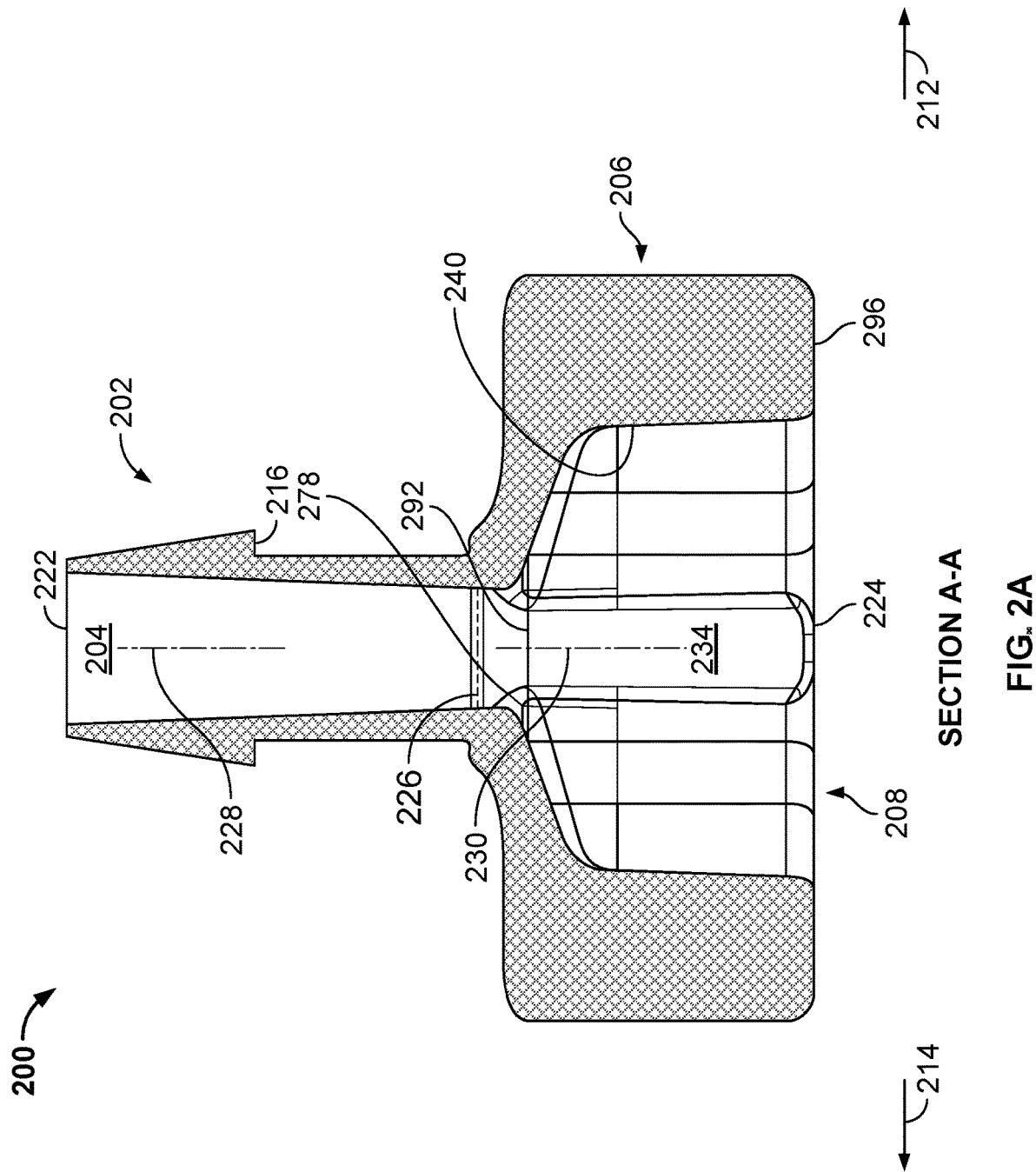

SECTION B-B

CONTROLLING A FLUID FLOW

CROSS-REFERENCE TO RELATED APPLICATION

This application claims priority under 35 U.S.C. § 119 to U.S. Provisional Patent Application Ser. No. 63/231,125, filed on Aug. 9, 2021, the entire contents of which are incorporated by reference herein.

TECHNICAL FIELD

This disclosure relates to fluid storage and transportation for medical devices.

BACKGROUND

Medical devices can be used to store and flow fluids such biopharmaceutical fluids. Medical devices can flow fluids to other medical devices for further processing or to a person for medical treatment. Medical devices must meet industry safety and cleanliness standards to keep the biopharmaceutical fluids free from contamination from the environment and the manufacturing process in order to safeguard the health of the person receiving the medical treatment.

SUMMARY

This disclosure describes technologies related to a device, a system, and a method for controlling a flow of a biopharmaceutical fluid with a biopharmaceutical flow port.

In an example implementation, a biopharmaceutical flow port includes a hose barb and an elliptic body. The hose barb includes a bore. The elliptic body is coupled to the hose barb. The elliptic body includes a flow passage, a first edge, and a second edge. The flow passage is fluidly coupled to the bore. The first edge extends from the elliptic body away from the flow passage in a first direction. The second edge extends from the elliptic body away from the flow passage in a second direction opposite the first direction.

In an aspect combinable with the example implementation, the hose barb is integrally formed with the elliptic body.

In another aspect combinable with any of the previous aspects, the hose barb includes a ridge configured to secure a conduit into fluid communication with the bore.

In another aspect combinable with any of the previous aspects, the flow passage is defined at least partially by a first flow passage portion having an elliptical cross-section and a second flow passage portion having a circular cross-section.

In another aspect combinable with any of the previous aspects, the first flow passage portion and second flow passage portion are fluidly coupled.

In another aspect combinable with any of the previous aspects, a radial centerline of the bore coincides with a radial centerline of the second flow passage portion.

In another aspect combinable with any of the previous aspects, the second flow passage portion meets the bore at a rounded shoulder of an inner surface of the elliptic body defined by the flow passage.

In another aspect combinable with any of the previous aspects, the flow passage includes a frusto-conical inner surface portion of the elliptic body.

In another aspect combinable with any of the previous aspects, the frusto-conical inner surface portion includes a transition from the flow passage to the bore.

In another aspect combinable with any of the previous aspects, the bore and the second flow passage portion include a contiguous opening.

In another aspect combinable with any of the previous aspects, the flow passage has a circular cross-section.

In another aspect combinable with any of the previous aspects, a diameter of the circular cross-section flow passage and a diameter of bore are substantially equal.

In another aspect combinable with any of the previous aspects, a radial centerline of the bore coincides with a radial centerline of the flow passage.

In another aspect combinable with any of the previous aspects, flow passage meets the bore at a rounded shoulder of an inner surface of the elliptic body defined by the flow passage.

In another aspect combinable with any of the previous aspects, the flow passage includes a frusto-conical inner surface portion of the elliptic body.

In another aspect combinable with any of the previous aspects, the frusto-conical inner surface portion includes a transition from the flow passage to the bore.

In another aspect combinable with any of the previous aspects, the flow passage is defined at least partially by a first flow passage portion having a rounded rectangular cross-section and a second flow passage portion having a circular cross-section.

In another aspect combinable with any of the previous aspects, the first flow passage portion and second flow passage portion are fluidly coupled.

In another aspect combinable with any of the previous aspects, a radial centerline of the bore coincides with a radial centerline of the second flow passage portion.

In another aspect combinable with any of the previous aspects, the second flow passage portion meets the bore at a rounded shoulder of an inner surface of the elliptic body defined by the flow passage.

In another aspect combinable with any of the previous aspects, a major dimension and a minor dimension of the rounded rectangular cross-section decrease from a first end of the elliptic body to a second end of the elliptic body and the second end of the elliptic body is closer to the hose barb that the first end.

In another aspect combinable with any of the previous aspects, an inner surface of the elliptic body includes a transition from the flow passage to the bore.

In another aspect combinable with any of the previous aspects, the bore and the second flow passage portion have a contiguous opening.

In another aspect combinable with any of the previous aspects, the second flow passage extends through the first flow passage into the hose barb.

In another aspect combinable with any of the previous aspects, the circular cross-section extends outside the rounded rectangular cross-section.

Another aspect combinable with any of the previous aspects further includes a ribbed portion formed on an outer surface of the elliptic body, and the ribbed portion extends across the outer surface of the elliptic body from each of the first and second edges toward the hose barb.

In another aspect combinable with any of the previous aspects, the first edge and the second edge are integrally formed with the elliptic body.

In another aspect combinable with any of the previous aspects, each of the first and second edges include a first curved surface and a second curved surface that mirrors the first curved surface and meets the first curved surface at an edge.

In another aspect combinable with any of the previous aspects, the bore is defined by a first radial dimension at a first end near the elliptic body and a second radial dimension larger than the first radial dimension at a second end opposite the first end.

Another aspect combinable with any of the previous aspects further includes tabs that extend from the elliptic body.

In another example implementation, a biopharmaceutical liquid container assembly includes a biopharmaceutical liquid container and a biopharmaceutical flow port. The biopharmaceutical liquid container includes an opening. The biopharmaceutical flow port includes any of the aspects previously described. The biopharmaceutical flow port is coupled to the biopharmaceutical liquid container within the opening and in fluid communication with a volume of the biopharmaceutical liquid container.

In another aspect combinable with any of the previous aspects, the biopharmaceutical liquid container includes a first sheet and a second sheet. The first sheet includes a first outer edge. The second sheet includes a second outer edge sealed to the first outer edge.

In another aspect combinable with any of the previous aspects, the flow port includes a first flow port and the opening is a first opening. The biopharmaceutical liquid container further includes a second opening and the biopharmaceutical liquid container assembly further includes a second flow port including any of the aspects previously described.

In another aspect combinable with any of the previous aspects, the biopharmaceutical liquid container is plastic.

In another example implementation, a biopharmaceutical liquid manifold system includes a first biopharmaceutical liquid container assembly including any of the aspects previously described, a second biopharmaceutical liquid container assembly including any of the aspects previously described, and a manifold assembly including at least one conduit fluidly coupled to the first biopharmaceutical liquid container and the second biopharmaceutical liquid container.

In another aspect combinable with any of the previous aspects, the first biopharmaceutical liquid container is coupled to the at least one conduit by a first hose barb of a first flow port and the second biopharmaceutical liquid container is coupled to the at least one conduit by a second hose barb of a second flow port.

In another example implementation, a biopharmaceutical liquid container manufacturing method includes placing at least a portion of an elliptic body of a flow port in contact with a first sheet. The flow port includes a hose barb and an elliptic body. The hose barb includes a bore. The elliptic body is coupled to the hose barb. The elliptic body includes a flow passage, a first edge, and a second edge. The flow passage is fluidly coupled to the bore. The first edge extends from the elliptic body away from the flow passage in a first direction. The second edge extends from the elliptic body away from the flow passage in a second direction opposite the first direction. The biopharmaceutical liquid container manufacturing method includes placing a second sheet on at least another portion of the elliptic body of the flow port and the first sheet, and the sealing the second sheet to the flow port and the first sheet.

In an aspect combinable with the example implementation, the first sheet and the second sheet each comprise a thermoplastic.

In another aspect combinable with any of the previous aspects, sealing the second sheet to the flow port and the first sheet includes heating at least one of the second sheet, the flow port, or the first sheet and heat sealing the second sheet to the flow port and the first sheet.

Another aspect further combinable with any of the previous aspects further includes, prior to sealing the second sheet to the flow port and the first sheet, compressing the second sheet, the flow port, and the first sheet together.

In another aspect combinable with any of the previous aspects, compressing the second sheet, the flow port, and the first sheet together includes maximizing an area of contact between the first sheet and the portion of the elliptic body of the flow port and maximizing an area of contact between the second sheet and the another portion of the elliptic body of the flow port.

In another aspect combinable with any of the previous aspects, the portion of the elliptic body of the flow port includes a first outer surface of the elliptic body that includes a first outer surface of the first edge and a first outer surface of the second edge, and the another portion of the elliptic body of the flow port includes a second outer surface of the elliptic body that includes a second outer surface of the first edge and a second outer surface of the second edge, the second outer surface opposite the first outer surface.

Another aspect further combinable with any of the previous aspects further includes aligning a first tab of the flow port with an edge of the first sheet and aligning a second tab of the flow port with an edge of the second sheet.

Another aspect further combinable with any of the previous aspects further includes forming the flow port.

In another aspect combinable with any of the previous aspects, forming the flow port includes injecting a plastic into a negative mold of the flow port.

In another aspect combinable with any of the previous aspects, the steps of placing at least the portion of the elliptic body of the flow port in contact with the first sheet, placing the second sheet on at least the another portion of the elliptic body of the flow port and the first sheet, and sealing the second sheet to the flow port and the first sheet are completed without human contact with the hose barb.

Example implementations for controlling a biopharmaceutical fluid according to the present disclosure may include one, some, or all of the following features. For example, controlling the fluid with the biopharmaceutical flow port according to the present disclosure may increase the cleanliness of the biopharmaceutical fluid stored in the medical device. Specifically, portions of the raw materials which will be used to construct a biopharmaceutical liquid container with the biopharmaceutical flow port may no longer need to be touched. Reducing or eliminating the number of times raw materials are touched may reduce contamination from the environment and the manufacturing process. Additionally, the biopharmaceutical flow port of the present disclosure can be positioned, in other words, sandwiched, along the edges of two sheets used to manufacture the biopharmaceutical liquid container. As another example, controlling the fluid with the biopharmaceutical flow port according to the present disclosure may improve the seal quality between the biopharmaceutical flow port and the biopharmaceutical liquid container. The edges of the elliptic body may improve the seal quality. For example, reducing the sharp transitions between surfaces of the elliptic body and the edges may improve the quality of the seal. For example, when the projected direction orthogonal to an outer surface of the elliptic body is aligned with a clamping direction of the sealing equipment, the quality of the seal may be improved. Also, the alignment tabs of the biopharmaceutical flow port may improve the positioning of the biopharmaceutical flow port in the biopharmaceutical liquid container during the manufacturing process, which may improve the quality of the seal and may reduce contamination. Improving the quality of the seal may reduce fluid leakage pathways. As a further example, controlling the fluid with the biopharmaceutical flow port according to the present disclosure may reduce manufacturing scrap rates of the biopharmaceutical liquid container. An external surface of the biopharmaceutical flow port may align to the edges of the sheets which improves biopharmaceutical flow port placement consistency and reduce manufacturing scrap rates. As a further example, controlling the fluid with the biopharmaceutical flow port according to the present disclosure may reduce manufacturing time. Using the external surface of the biopharmaceutical flow port to align to the edges of the sheets may reduce the time to properly align the biopharmaceutical flow port to the sheets, which may reduce the overall manufacturing time per biopharmaceutical liquid container. As still yet another example, controlling the fluid with the biopharmaceutical flow port according to the present disclosure may decrease the instances of biopharmaceutical liquid container failure during use. Improving the seal quality during manufacturing may result in fewer biopharmaceutical liquid container failures when the biopharmaceutical liquid containers are filled.

As another example, controlling the fluid with the biopharmaceutical flow port according to the present disclosure may improve biopharmaceutical liquid container drainage. When the biopharmaceutical liquid container is placed in a hanging position or utilized in a hands-off dispensing process and the biopharmaceutical fluid transfer is initiated, the biopharmaceutical fluid can drain more completely from the biopharmaceutical liquid container because the biopharmaceutical flow port positioned on the edge of the biopharmaceutical liquid container. As a further example, controlling the fluid with the biopharmaceutical flow port according to the present disclosure may increase a fluid transfer rate from the biopharmaceutical liquid container. The inner profile of the biopharmaceutical flow port may increase the fluid transfer rate increasing a cross-sectional diameter and decreasing flow turbulence by using a complex unstepped inner profile to flow the biopharmaceutical fluid from the biopharmaceutical liquid container through the biopharmaceutical flow port to another medical device or a person.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

FIG. 1B is a cross-section view of the elliptic body of the example implementation of the biopharmaceutical flow port of FIG. 1A.

FIG. 1C is a side cross-section view of the example implementation of the biopharmaceutical flow port of FIG. 1B.

FIG. 1G is another side cross-section view of the elliptic body of the example implementation of the biopharmaceutical flow port of FIG. 1A with a second flow passage.

FIG. 1H is a cross-section view of the elliptic body of the example implementation of the biopharmaceutical flow port of FIG. 1G with the second flow passage.

FIG. 1I is a cross-section view of the elliptic body of the example implementation of the biopharmaceutical flow port of FIG. 1G with a third flow passage.

FIG. 2A is a cross-section view of another example implementation of the biopharmaceutical flow port according to the present disclosure.

DETAILED DESCRIPTION

This disclosure describes technologies related to a device, a system and a method for controlling a fluid with a biopharmaceutical flow port. FIGS. 1A and 1D-1F are each a perspective view of a biopharmaceutical flow port 100 for controlling a fluid flow.

Figure 1A:
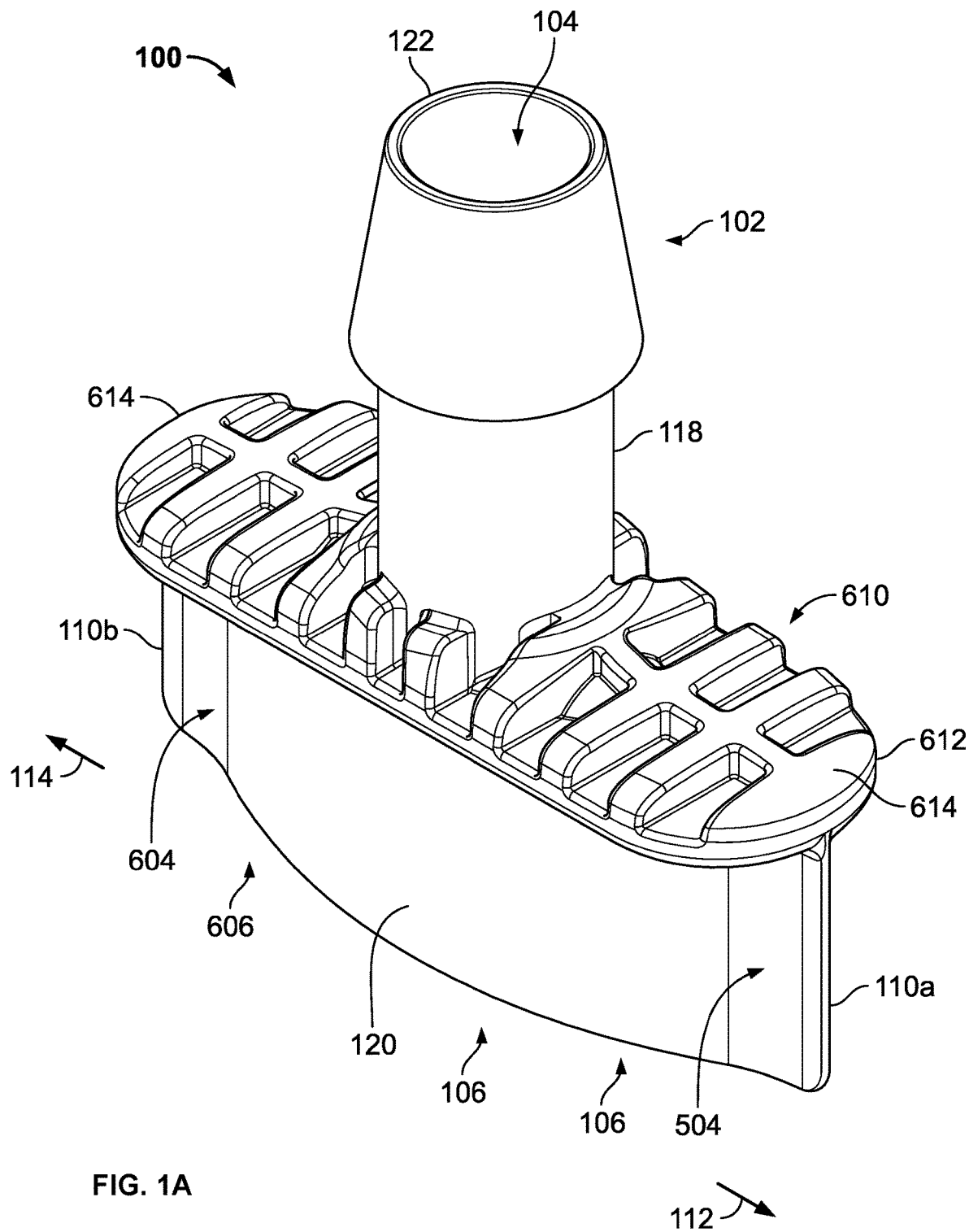
FIG. 1A is a perspective view of an example implementation of a biopharmaceutical flow port according to the present disclosure.
Figure 1D:
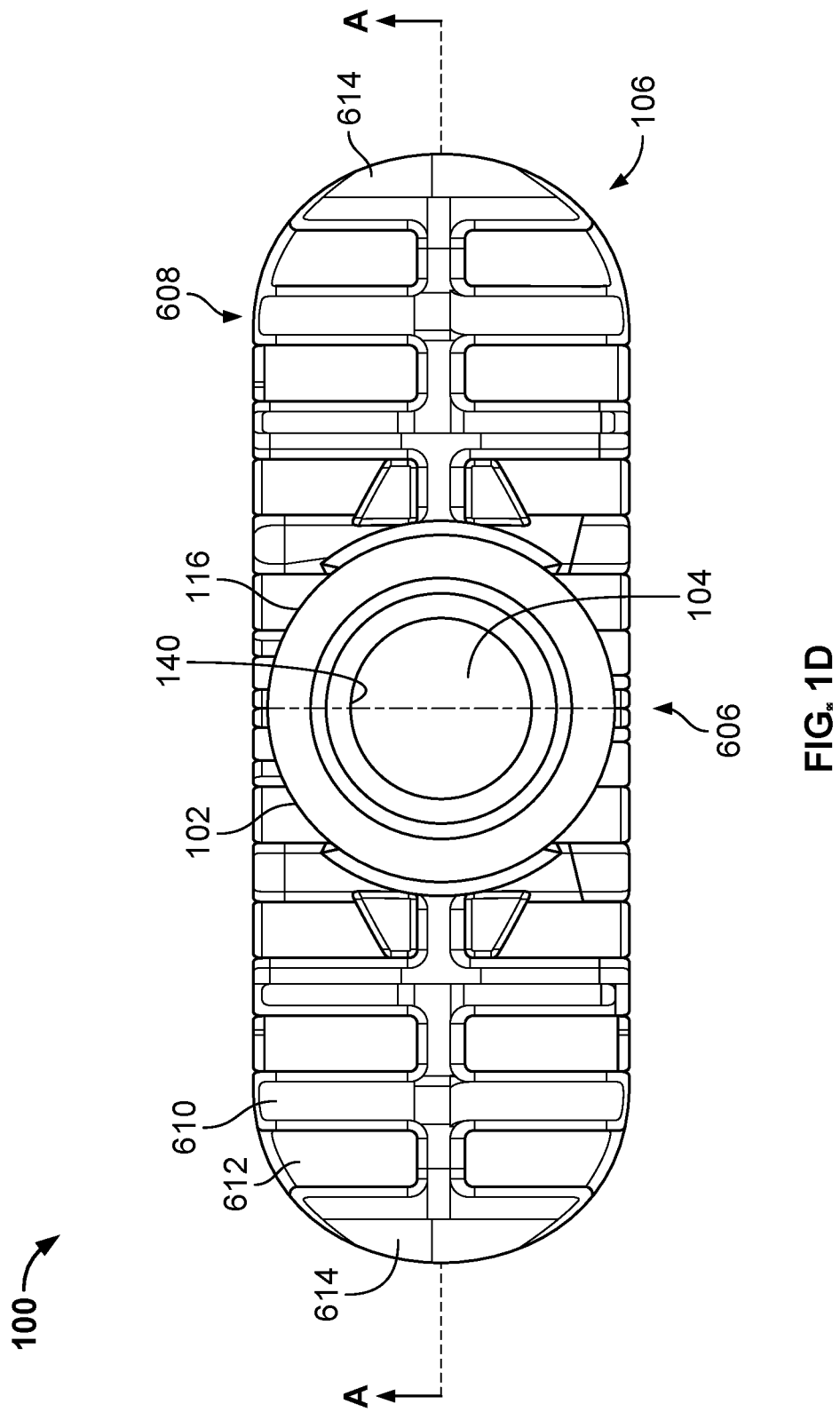
FIG. 1D is a side view of the example implementation of the biopharmaceutical flow port of FIG. 1A.

Generally, FIG. 1A illustrates an example implementation of the biopharmaceutical flow port 100 according to the present disclosure in which a biopharmaceutical fluid may be flowed. The biopharmaceutical flow port 100, in some aspects, includes a hose barb 102 to couple the biopharmaceutical flow port 100 to a hose (e.g., hose 302 of the biopharmaceutical liquid container assembly 300 shown in FIG. 3). The hose barb 102 has a bore 104 to conduct the biopharmaceutical fluid through the hose barb 102 and out an opening 122. Referring to FIG. 1A, in some aspects, the biopharmaceutical flow port 100 includes an elliptic body 106. Referring to FIGS. 1A and 3, the elliptic body 106 is coupled to the hose barb 102 to conduct the biopharmaceutical fluids from a biopharmaceutical liquid container 304 of the biopharmaceutical liquid container assembly 300 to the hose 302. FIG. 1B is a cross-section view of the elliptic body 106 of the biopharmaceutical flow port 100 of FIG. 1A. As shown in FIG. 1B, the elliptic body 106 has a flow passage 108 fluidly coupled to the bore 104. Referring to FIGS. 1A-1B, the elliptic body 106 has two edges 110a and 110b (a first edge 110a and a second edge 110b) extending from the elliptic body 106 away from the flow passage 108 in opposite directions as shown by a first arrow 112 and a second arrow 114, respectively. The elliptic body 106 and the two edges 110a and 110b define an outer surface 120. Referring to FIGS. 1A and 2, the outer surface 120 couples to the biopharmaceutical liquid container assembly 300.

The biopharmaceutical flow port 100 can be a plastic. For example, the plastic can be a low-density polyethylene plastic.

Figure 1E:
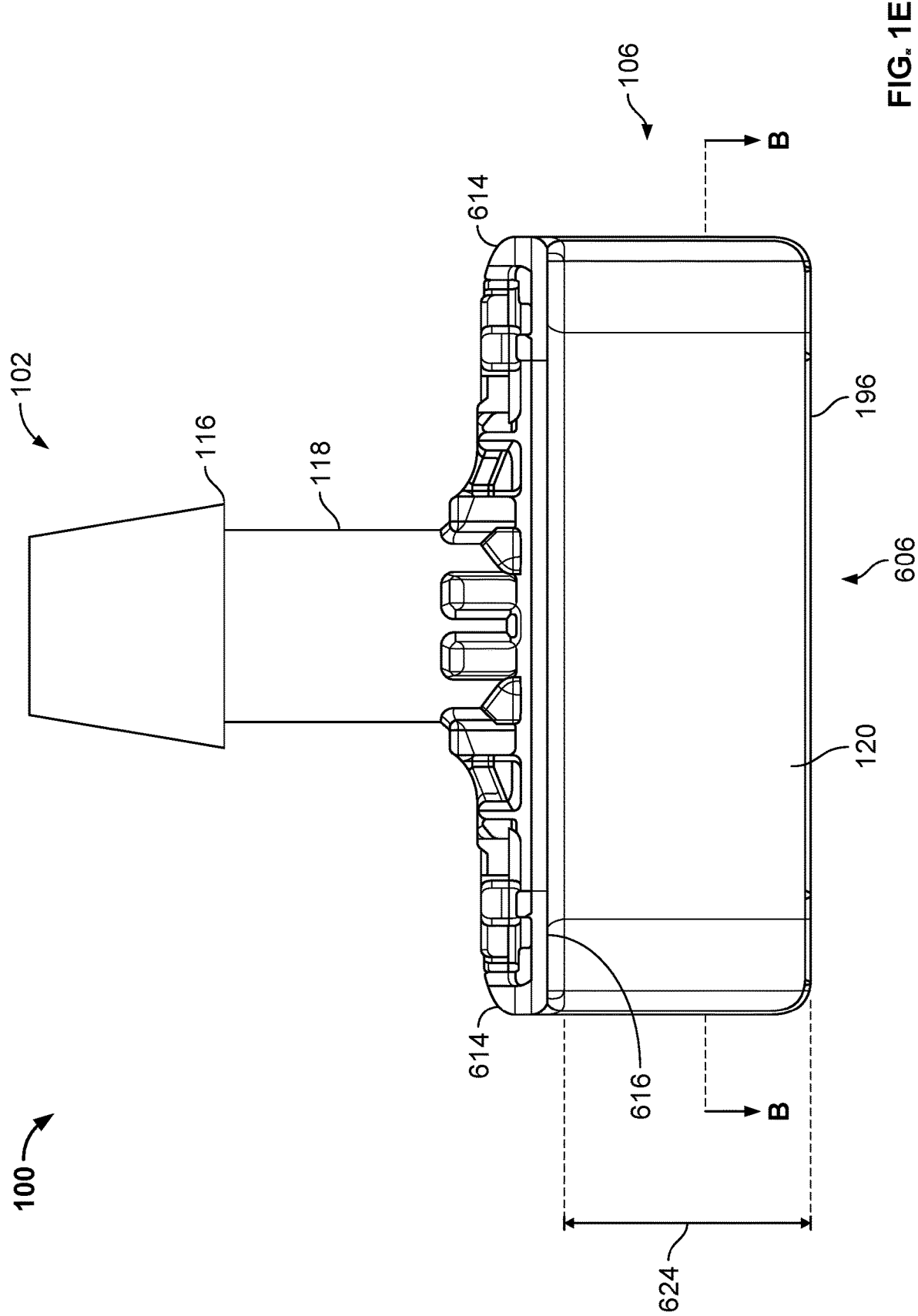
FIG. 1E is a front view of the example implementation of the biopharmaceutical flow port of FIG. 1A.

FIG. 1C is a side cross-section view of the biopharmaceutical flow port 100 of FIG. 1B. Referring to FIG. 1C, the elliptic body 106 has a length 620. The length 620 of the elliptic body 106 can be between 1 and 4 inches. As shown in FIG. 1C, the elliptic body 106 has a length 620 of 1.5 inches. The elliptic body 106 has a width 622. The width 622 of the elliptic body 106 can be between 0.3 and 2 inches. As shown in FIG. 1C, the elliptic body 106 has a width 622 of 0.375 inches. FIG. 1E is a front view of the biopharmaceutical flow port 100 of FIG. 1A. Referring to FIG. 1E, the elliptic body 106 has a height 624. The height 624 of the elliptic body 106 can be between 0.3 and 2 inches. As shown in FIG. 1E, the elliptic body 106 has a height 624 of 0.5 inches.

Referring to FIGS. 1A-1B and 1D-1F, the hose barb 102 is coupled to the elliptic body 106. In some aspects, the hose barb 102 is integrally formed with the elliptic body 106. For example, during a manufacturing process, the biopharmaceutical flow port 100 can be formed by an injection molding process, a pressing process, a machining process, or a three-dimensional printing process, the hose barb 102 and the elliptic body 106 can be produced as a unitary body.

Alternatively, the hose barb 102 and the elliptic body 106 can be formed separately, then later joined together. For example, the hose barb 102 and the elliptic body 106 can include threads (not shown), which can couple the hose barb 102 to the elliptic body 106. For example, the hose barb 102 and the elliptic body 106 can be press fit (force or friction fit) together. For example, the hose barb 102 and the elliptic body 106 can be held together by an adhesive.

In some aspects, the hose barb 102 has a ridge 116 extending from an outer surface 118, as shown in FIG. 1A, to additionally couple the hose barb 102 to the hose 302, as shown in FIG. 3. In some aspects, the hose barb 102 includes multiple ridges 116 along the outer surface 118 (not shown). As shown in FIGS. 1A-1B, the ridge 116 is triangular. Alternatively or in addition, the ridge 116 can be semi-circular, square, or another geometric shape. A clamp (not shown), such as a hose clamp, an ear clamp, or a snap ring, can be used to additionally couple the hose barb 102 to the hose 302.

Referring to FIG. 1C, the elliptic body 106 has an inner surface 140 which defines the fluid passage 108 to direct the flow of the biopharmaceutical fluid. Referring to FIGS. 1A-1C, the flow passage 108 of the elliptic body 106 is fluidly coupled to the bore 104 of the hose barb 102. Generally, the flow passage 108 receives the biopharmaceutical fluid from the biopharmaceutical liquid container assembly 300 at an opening 124. The flow passage 108 is fluidly coupled to the bore 104 at cross-section 126. The flow passage 108 conducts the biopharmaceutical fluid from the opening 124 through the cross-section 126 to the bore 104, which then conducts the biopharmaceutical fluid out opening 122. In some aspects, however, the flow of the biopharmaceutical fluid may be in reverse, that is, the flow of the biopharmaceutical fluid can be from the opening 122 through the bore 104 into the flow passage 108 and then out the opening 124. A diameter 148 of the opening 122 can be between 0.015 and 1.25 inches. For example, as shown in FIG. 1B, the diameter 148 of the opening 122 can be 0.31 inches.

In some aspects, the cross-section 126 and the opening 122 define the bore 104. The cross-section 126 is defined by a diameter 150 a first end 602 near the elliptic body 106. The opening 122 with the diameter 148 can be larger than the diameter 150.

The opening 124 is on a surface 196 of the elliptic body. A shoulder 198 can be between the opening 124 and the flow passage 108 to control the flow of the biopharmaceutical fluid.

The bore 104 has a radial centerline 128. The flow passage 108 has a radial centerline 130. In some aspects, the radial centerline 128 of the bore 104 coincides with the radial centerline 130 of the flow passage 108. However, in other aspects, the radial centerline 128 of the bore 104 may differ from the radial centerline 130 of the flow passage 108.

Referring to FIG. 1B, in some aspects, the flow passage 108 has a first flow passage portion 132 and a second flow passage portion 134. As shown in FIG. 1B, the first flow passage portion 132 has a rounded rectangular cross-section 136. The first flow passage portion 132 extends from the opening 124 to the second flow passage portion 134. The opening 124 has a rounded rectangular cross-section 136. The second flow passage portion 134 has a circular cross-section. The second flow passage portion 134 is fluidly coupled to the hose barb 102 at cross-section 126. The bore 104 and the second flow passage portion 134 form a contiguous opening at cross-section 126.

The rounded rectangle cross-section 136 has a length 142 (a major dimension) and a width 144 (a minor dimension). The width 144 corresponds to a radius 146 of a circle which define the rounded sides of the width of the rounded rectangular cross-section 136. For example, the length 142 can be between 0.12 and 3.5 inches. For example, the width 144 can be between 0.12 and 1.25 inches. For example, the radius 146 can be between 0.015 inches and a straight section with no radius. For example, as shown in FIG. 1B, the length 142 can be 0.3 inches, the width 144 can be 0.18 inches, and the radius 146 can be 0.16 inches. In some aspects, the length 142, the width 144, and the radius 146 of the rounded rectangular cross-section 136 are constant across the first flow passage portion 132. In other aspects, the length 142, the width 144, and the radius 146 of the rounded rectangle cross-section can increase, decrease, or both increase and decrease across the first flow passage portion 132. For example, the flow passage 108 can have a frusto-conical inner surface 140 defined in the elliptic body 106.

Referring to FIG. 1B, the first flow passage portion 132 is fluidly coupled to the second flow passage portion 134. The first flow passage portion 132 transitions to the second flow passage portion 134 at a shoulder 138. Alternatively, the first flow passage portion 132 can transition to the second flow passage portion 134 across a frusto-conical portion (not shown) of the inner surface 140. The second flow passage portion 134 has a circular cross-section. The second flow passage portion 134 circular cross section has the diameter 150, which corresponds to the cross-section 126. The diameter 150 can be between 0.05 and 0.35 inches. For example, as shown in FIG. 1B, the diameter 150 is 0.24 inches. In some aspects, the transition of the inner surface 140 is generally smooth as compared to the shoulder 138 transition between the first flow passage portion 132 and the second flow passage portion 134.

FIG. 1G is another side cross-section view of the elliptic body 106 of the biopharmaceutical flow port 100 of FIG. 1A with a second flow passage 152. FIG. 1H is a cross-section view of the elliptic body 106 of the biopharmaceutical flow port 100 of FIG. 1G with a with the second flow passage 152. Referring to FIGS. 1G-1H, in some aspects, the second flow passage 152 has a first flow passage portion 154 and a second flow passage portion 156. As shown in FIGS. 1G-1H, the first flow passage portion 152 has a rounded rectangular cross-section 158 with a circular cross-section 160 extending outside the rounded rectangular cross-section 158. A diameter 170 of the circular cross-section 160 can be between 0.015 and 1.25 inches.

The first flow passage portion 154 extends from the opening 124 to cross-section 162. The opening 124 has a rounded rectangular cross-section with the circular cross-section 160 extending outside the rectangular cross-section 158. The second flow passage portion 156 has the circular cross-section 160. The second flow passage portion 156 extends from the opening 124 through the first flow passage portion 154 past cross-section 162. At cross-section 162, an inner diameter 164 of the second flow passage portion 156 increases to equal the diameter 148 of the hose barb 102. The increase of the inner diameter 164 of the second flow passage portion 156 to the diameter 148 of the hose barb 102 defines a shoulder 168. Alternatively, the increase of the inner diameter 164 of the second flow passage portion 156 to the diameter 148 of the hose barb 102 can define a frusto-conical surface (not shown). The bore 104 and the second flow passage portion 156 form a contiguous opening at cross-section 126 across the shoulder 168. Referring to FIG. 1H, the diameter 148 of the opening 122 is 0.187 inches.

FIG. 1I is a cross-section view of the elliptic body 106 of the biopharmaceutical flow port 100 of FIG. 1G with a third flow passage 172. The third flow passage 172 is generally similar to the second flow passage 152 previously described. Referring to FIGS. 1G and 1I, in some aspects, the third flow passage 152 has the first flow passage portion 154 and the second flow passage portion 156. As shown in FIGS. 1G and 1I, the first flow passage portion 152 has the rounded rectangular cross-section 158 with a circular cross-section 160 extending outside the rounded rectangular cross-section 158. A diameter 170 of the circular cross-section 160 can be between 0.015 and 1.25 inches.

Referring to FIG. 1I, the first flow passage portion 154 extends from the opening 124 and terminates at cross-section 162. The opening 124 has a rounded rectangular cross-section with the circular cross-section 160 extending outside the rectangular cross-section 158. The second flow passage portion 156 has the circular cross-section 160. The second flow passage portion 156 extends from the opening 124 and terminates in the first flow passage portion 154 at cross-section 174 before cross-section 162. Between cross-section 174 and cross-section 162, the rounded rectangular cross-section 158 (the length 142 and the width 144) blend to form a circular cross-section 176 with a diameter 618.

A shoulder 178 extends from the circular cross-section 176 to meet the bore 104 of the hose barb 102. The bore 104 and the shoulder 178 form a contiguous opening at cross-section 126 across the shoulder 168. Referring to FIG. 1H, the diameter 148 of the opening 122 is 0.096 inches.

Figure 2B:
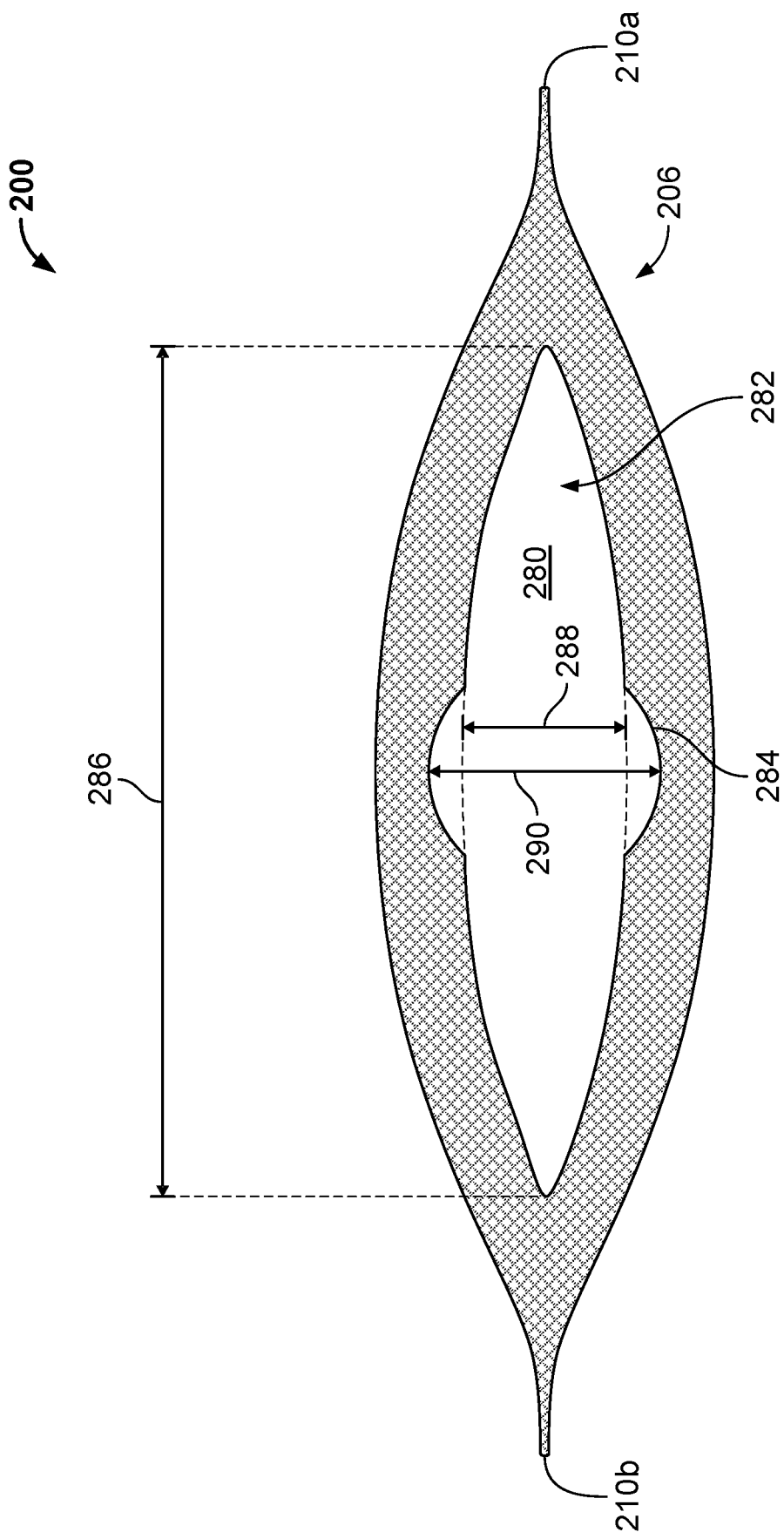
FIG. 2B is another side cross-section view of an elliptic body of the example implementation of the biopharmaceutical flow port of FIG. 2A.
Figure 2C:
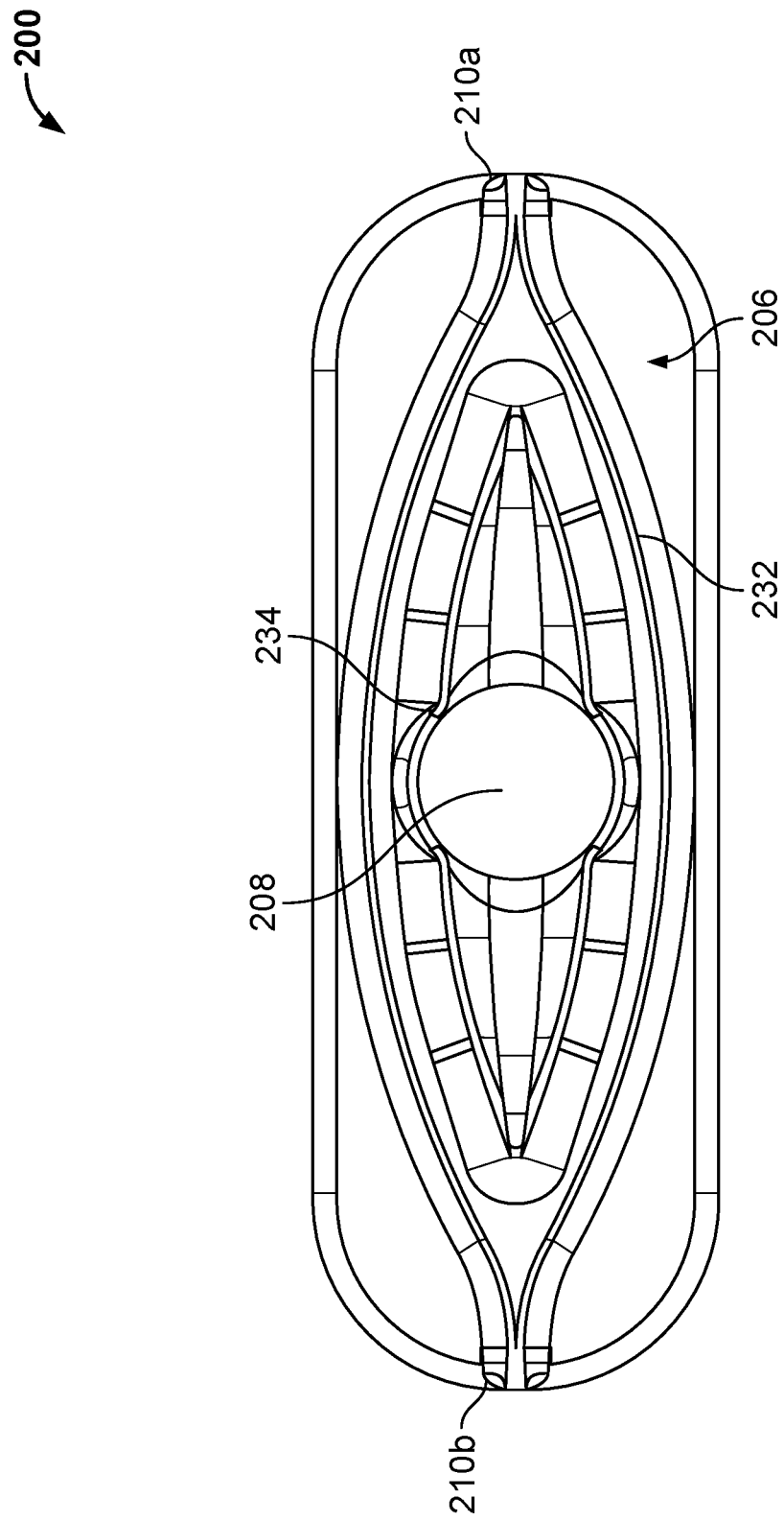
FIG. 2C is a bottom view of the example implementation of the biopharmaceutical flow port of FIG. 2A.
Figure 3:
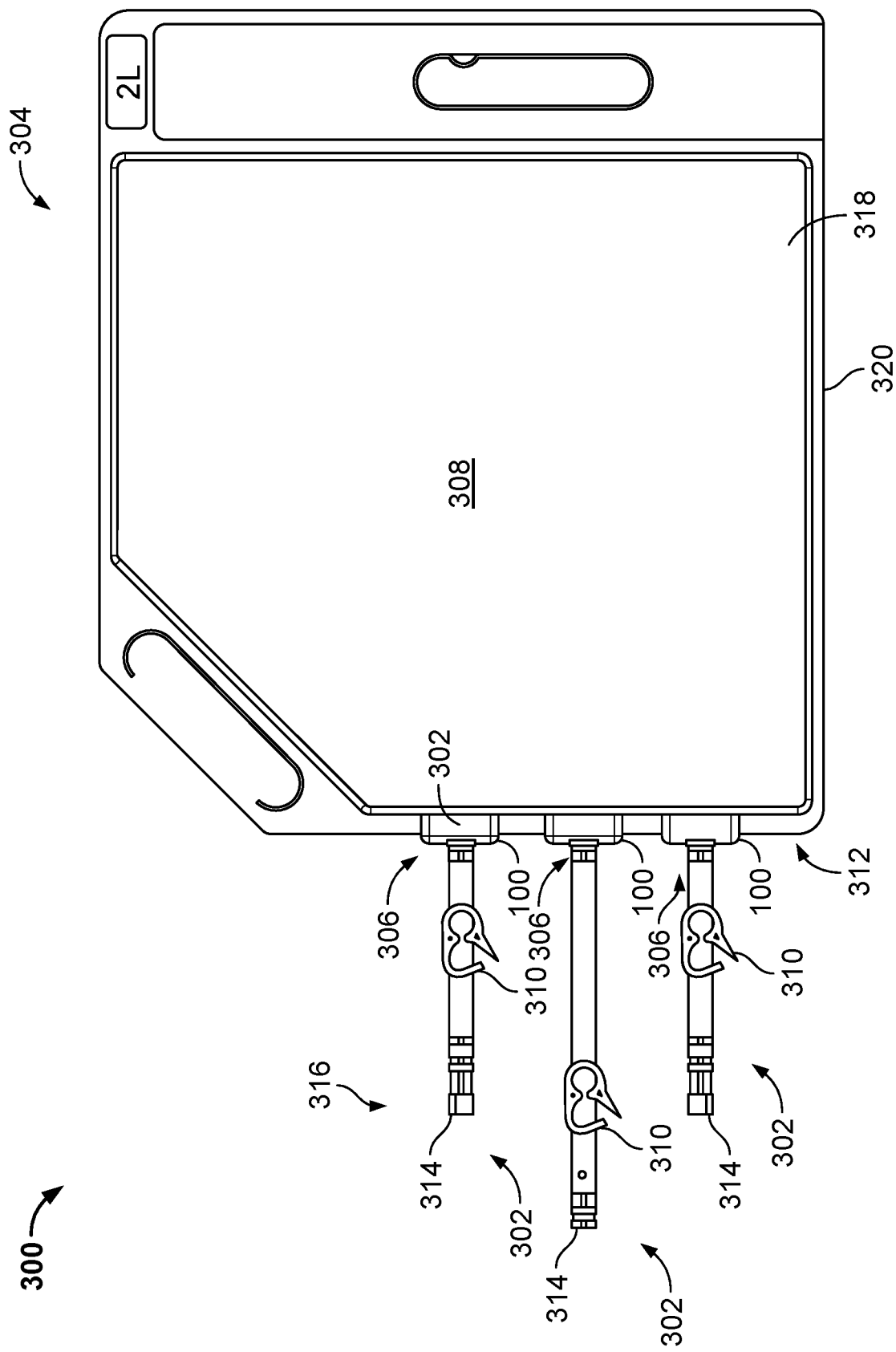
FIG. 3 is a schematic diagram of an example implementation of a biopharmaceutical liquid container assembly according to the present disclosure.

FIG. 2A is a cross-section view of another example implementation of a biopharmaceutical flow port 200 according to the present disclosure. FIGS. 2B and 2C are a side cross-section view and a bottom view of the biopharmaceutical flow port 200, respectively, of FIG. 2A. The biopharmaceutical flow port 200, in some aspects, can be generally similar to the biopharmaceutical flow port 100 previously described.

Generally, FIG. 2A illustrates one implementation of the biopharmaceutical flow port 200 according to the present disclosure in which the biopharmaceutical fluid may be flowed. The biopharmaceutical flow port 200 includes a hose barb 202 to couple the biopharmaceutical flow port 200 (e.g., in place of the flow port 100) to a hose 302 of the biopharmaceutical liquid container assembly 300, as shown in FIGS. 2A and 3. The hose barb 202 has a bore 204 to conduct the biopharmaceutical fluid through the hose barb 202 and out an opening 222. Referring to FIG. 2B-2C, the biopharmaceutical flow port 200 includes an elliptic body 206. Referring to FIGS. 2A and 3, the elliptic body 206 is coupled to the hose barb 202 to conduct the biopharmaceutical fluids from a biopharmaceutical liquid container 304 of the biopharmaceutical liquid container assembly 300 to the hose 302. As shown in FIG. 2A-2B, the elliptic body 206 has a flow passage 208 fluidly coupled to the bore 204. Referring to FIGS. 2A-2C, the elliptic body 206 has two edges 210a and 210b (a first edge 210a and a second edge 210b) extending from the elliptic body 206 away from the flow passage 208 in opposite directions as shown by a first arrow 212 and a second arrow 214, respectively. The elliptic body 206 and the two edges 210a and 210b define an outer surface 220. Referring to FIGS. 2B-2C and 3, the outer surface 220 couples to the biopharmaceutical liquid container assembly 300.

Referring to FIG. 2B-2C, in some aspects, the flow passage 208 has a first flow passage portion 232 and a second flow passage portion 234. As shown in FIG. 2B, the first flow passage portion 232 has a rounded rectangular cross-section 236. The first flow passage portion 232 extends from the opening 224 to the second flow passage portion 234. The opening 224 has an elliptical cross-section 236. The first flow passage portion 232 with the elliptical cross-section is fluidly coupled to the second flow passage portion 234 having the circular cross-section. The second flow passage portion 234 having the circular cross-section passes through the first flow passage portion 232 with the elliptical cross-section. The first flow passage portion 232 with the elliptical cross-section and the second flow passage portion 234 having the circular cross-section converge at cross-section 292.

The second flow passage portion 234 is fluidly coupled to the hose barb 202 at cross-section 226. The bore 204 and the second flow passage portion 234 form a contiguous opening at cross-section 226. The second flow passage portion 234 having the circular cross-section continues from cross-section 292 to connect to the bore 204 at a rounded shoulder 278. The rounded shoulder 278 is on the inner surface 240 of the elliptic body 206 which defines the flow passage 208. The bore 204 and the second flow passage portion 234 having the circular cross-section are a contiguous opening.

The first flow passage portion 232 with the elliptical cross-section has a length 286 (a major dimension) and a width 288 (a minor dimension). For example, the length 286 can be between 0.015 and 3 inches. For example, the width 288 can be between 0.01 and 1.25 inches. The second flow passage portion 234 with the circular cross-section has a diameter 290. The diameter 290 can be between 0.015 and 1.25 inches. For example, as shown in FIG. 2B, the length 286 is 0.93 inches, the width 288 is 0.19 inches, and the diameter 290 is 0.26 inches.

In some aspects, the flow passage 108 has a circular cross-section (not shown). The flow passage 108 with the circular cross-section has a diameter. The flow passage 108 with the circular cross-section is fluidly coupled to the bore 104. Sometimes, the diameter of the circular cross-section flow passage 108 and a diameter 148 of bore 104 are substantially equal. In other cases, the diameter of the circular cross-section flow passage 108 and a diameter 148 of bore 104 can differ. When the diameter of the circular cross-section flow passage 108 and a diameter 148 of bore 104 differ, the flow passage 108 with the circular cross-section can transition to the bore 104 by a rounded shoulder or a frusto-conical surface.

Referring to FIGS. 1A-1C, 1E-1G, and FIG. 3, the two edges 110a and 110b extend from the elliptic body 106 away from the flow passage 108 in opposite directions (the first arrow 112 and the second arrow 114), respectively. The elliptic body 106 and the two edges 110a and 110b define the outer surface 120 which couples the biopharmaceutical flow port 100 to the biopharmaceutical liquid container assembly 300. In some aspects, first edge 110a and the second edge 110b are integrally formed with the elliptic body 106.

Referring to FIGS. 1A, 1C, 1E, and 1F, in some aspects, curved portions 604 can couple the edges 110a and 110b to the elliptic body on the outer surface 120. In some aspects, the curved portions 604 on either side 606 and 608 of the elliptic body mirror each other and meet at the edges 110a and 110b.

Referring to FIGS. 1A and 1D-1F, in some aspects, the biopharmaceutical flow port 100 has a ribbed portion 610 formed on an outer surface 612 of the elliptic body 106. The ribbed portion 610 extends across the outer surface 612 of the elliptic body 106 from the edges 110a and 110b toward the hose barb 102. The ribbed portion 610 can increase the structural rigidity of the elliptic body 106, improving the seal quality. The ribbed portion 610 can be injection molded without excessive sinks or voids in the part.

Referring to FIGS. 1A and 1D-1F, in some aspects, the biopharmaceutical flow port 100 has tabs 614 that extend from the elliptic body 106. A person (not shown) can grasp the tabs 614 to place the biopharmaceutical flow port 100 in between two sheets (described later in reference to FIG. 3) to manufacture the biopharmaceutical liquid container assembly 300 (described later in reference to FIGS. 3 and 5) to reduce contamination during the manufacturing process. Additionally, the tabs 614 can align the biopharmaceutical flow port 100 in manufacturing fixtures (not shown).

Figure 1F:
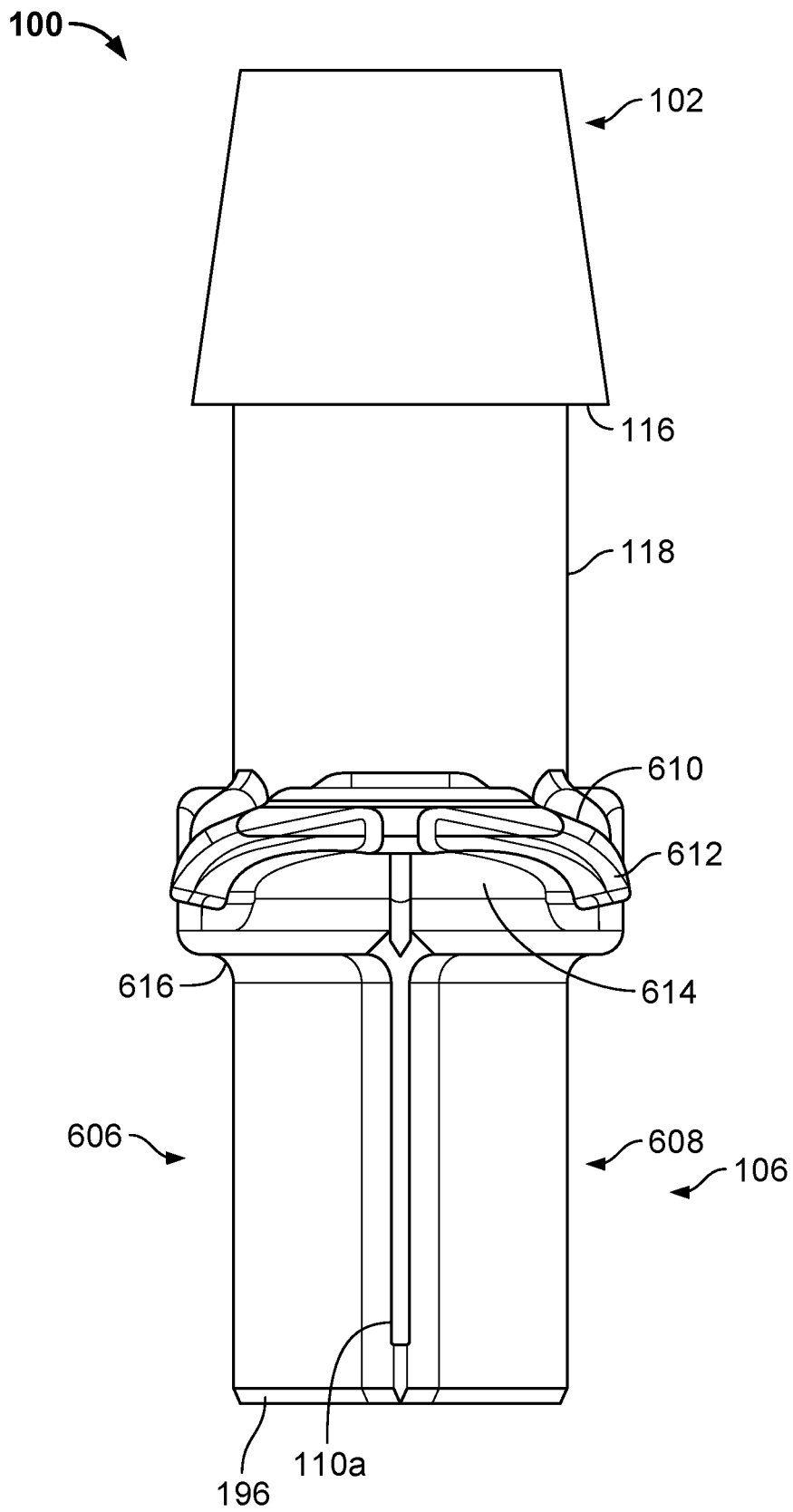
FIG. 1F is a top view of the example implementation of the biopharmaceutical flow port of FIG. 1A.

Referring to FIG. 1E-1F, in some aspects, the biopharmaceutical flow port 100 has a surface 616. The surface 616 is coupled to the elliptic body 106 and extends from the elliptic body 106. The surface 616 can be substantially perpendicular to the outer surface 120 of the elliptic body 106. The surface 616 can be used to align the biopharmaceutical flow port 100 to the biopharmaceutical liquid container assembly 300 during the manufacturing process (described later in reference to FIGS. 3 and 5).

FIG. 3 is a schematic diagram of the biopharmaceutical liquid container assembly 300 according to the present disclosure. Generally, FIG. 3 illustrates an example implementation of the biopharmaceutical liquid container assembly 300 according to the present disclosure from which the biopharmaceutical fluid may be flowed. The biopharmaceutical liquid container assembly 300 includes a biopharmaceutical liquid container 304 having an opening 306 and the biopharmaceutical flow port 100 (or 200 or another flow port according to the present disclosure) coupled to the biopharmaceutical liquid container 304 within the opening 306. The biopharmaceutical flow port 100 is in fluid communication with a volume 308 of the biopharmaceutical liquid container 304 through the bore 104.

Referring to FIG. 3, the assembly 300 has hoses 302 coupled to the hose barbs 102 of the biopharmaceutical flow ports 100 at a first end 312 of the hoses 302. The hoses 302 conduct the biopharmaceutical fluid to or from the biopharmaceutical liquid container 304 through the biopharmaceutical flow port 100. Flow control devices 310 can be placed in or on the hoses 302 to control the flow of the biopharmaceutical fluid. The hoses 302 can have fittings 314 coupled at a second end 316 of the hoses 302. The fittings 314 can couple to other fittings 314 and hoses 302.

The biopharmaceutical liquid container 304 has two sheets, a first sheet 318 and a second sheet 320. The first sheet 318 has an outer edge 322. The second sheet has an outer edge 324. The outer edge 324 of the second sheet 320 is sealed to the outer edge 322 of the first sheet 318. In some aspects, the outer edge 324 of the second sheet 320 is heat sealed to the outer edge 322 of the first sheet 318.

In some aspects, the sheets 318 and 320 are plastic. For example, the plastic can be polyethylene, polypropylene, or ethylene vinyl acetate.

Figure 4:
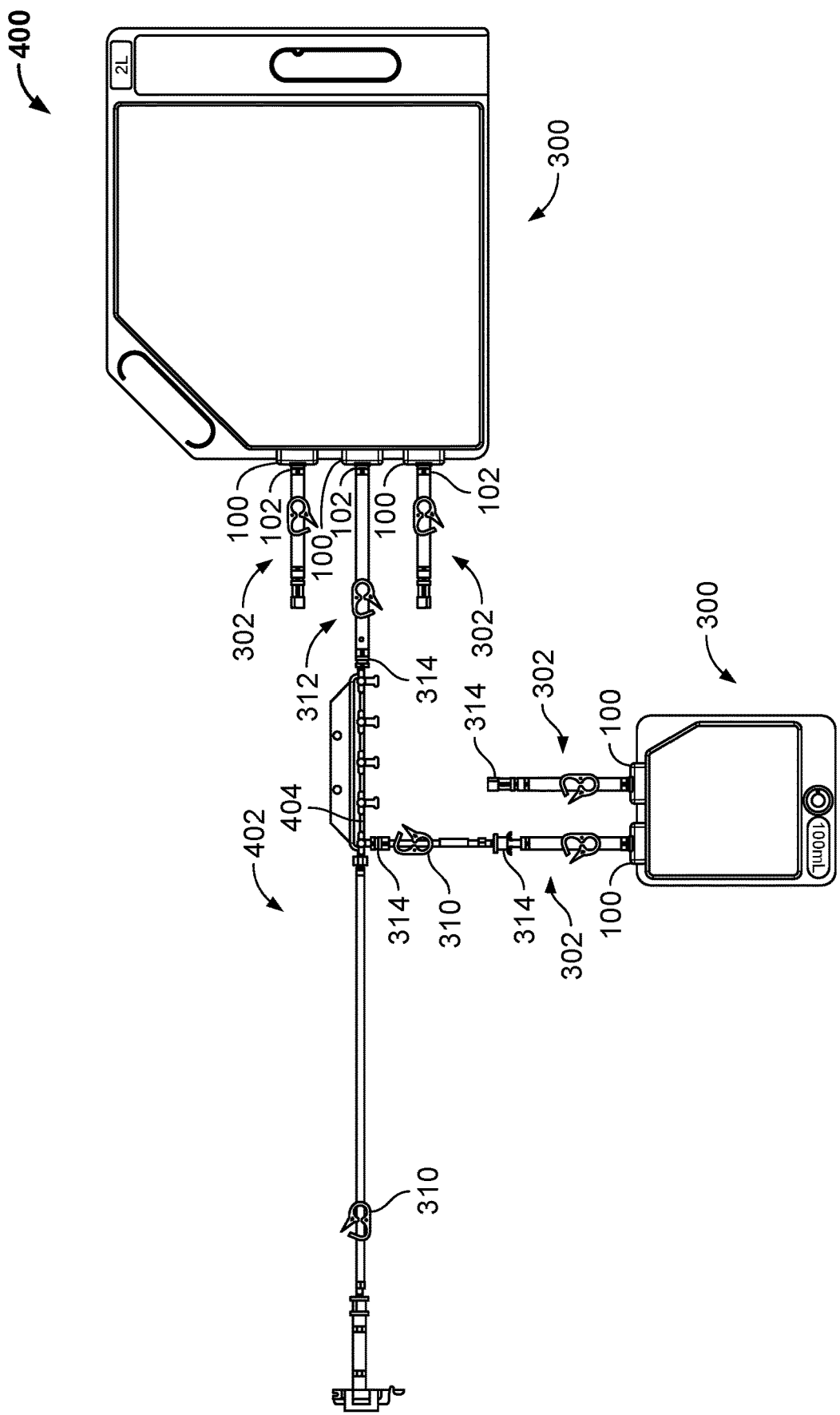
FIG. 4 is a schematic diagram of an example implementation of a biopharmaceutical liquid manifold system according to the present disclosure.

FIG. 4 is a schematic diagram of a biopharmaceutical liquid manifold system 400 according to the present disclosure. Generally, FIG. 4 illustrates an example implementation of the biopharmaceutical liquid manifold system 400 according to the present disclosure from which the biopharmaceutical fluid may be flowed. The biopharmaceutical liquid manifold system 400 includes one or more biopharmaceutical liquid containers 300 and a manifold assembly 402 having at least one conduit 404 fluidly coupled to each of the biopharmaceutical liquid containers 300 by the hoses 302 coupled to hose barbs of the biopharmaceutical flow ports installed in the one or more biopharmaceutical liquid containers 300 (such as flow ports 100, flow ports 200, or a combination thereof).

Figure 5:
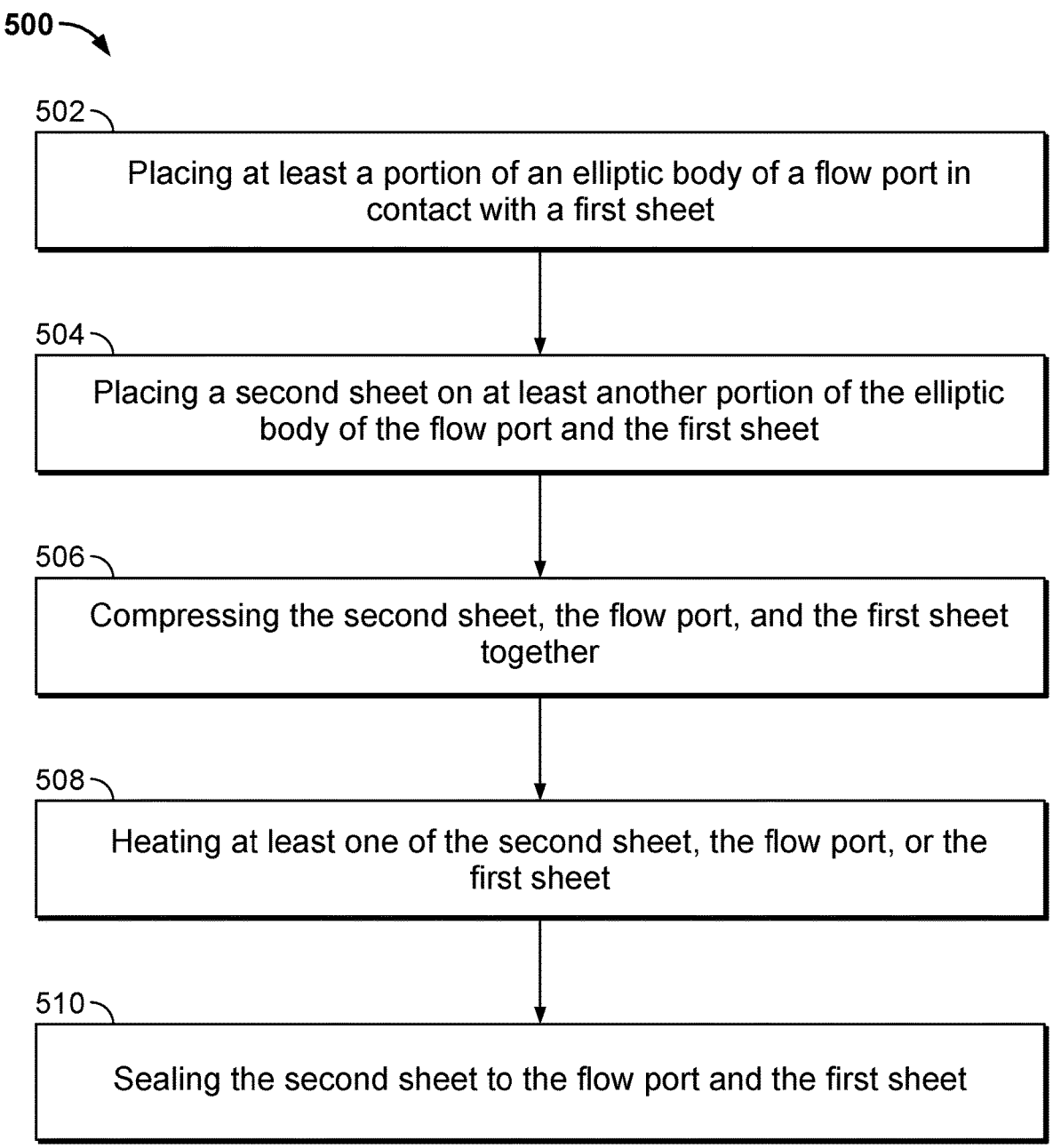
FIG. 5 is a flow chart that describes an example method of manufacturing a biopharmaceutical liquid container assembly with a biopharmaceutical flow port according to the present disclosure.

FIG. 5 illustrates a flow chart of method 500 for an example manufacturing operation for a biopharmaceutical liquid container, such as the biopharmaceutical liquid container assembly 300, for storing and flowing a biopharmaceutical fluid according to the present disclosure. Method 500 may begin at step 502, which includes placing at least a portion of an elliptic body of a flow port in contact with a first sheet. The flow port includes a hose barb having a bore. The elliptic body is coupled to the hose barb. The elliptic body includes a flow passage fluidly coupled to the bore, a first edge that extends from the elliptic body away from the flow passage in a first direction, and a second edge that extends from the elliptic body away from the flow passage in a second direction opposite the first direction. In some aspects, the portion of the elliptic body of the flow port includes a first outer surface of the elliptic body that includes a first outer surface of the first edge and a first outer surface of the second edge, and the another portion of the elliptic body of the flow port includes a second outer surface of the elliptic body that includes a second outer surface of the first edge and a second outer surface of the second edge with the second outer surface opposite the first outer surface. In some aspects, placing at least the portion of an elliptic body of the flow port in contact with the first sheet includes aligning a first tab of the flow port with an edge of the first sheet.

Method 500 may continue at step 504, which includes placing a second sheet on at least another portion of the elliptic body of the flow port and the first sheet. In some aspects, placing the second sheet on at least another portion of the elliptic body of the flow port and the first sheet includes aligning a second tab of the flow port with an edge of the second sheet. In some aspects, placing at least the portion of the elliptic body of the flow port in contact with the first sheet, placing the second sheet on at least the another portion of the elliptic body of the flow port and the first sheet, and sealing the second sheet to the flow port and the first sheet are completed without human contact with the hose barb.

Method 500 may continue at step 506, aspects, which includes compressing the second sheet, the flow port, and the first sheet together. In some aspects, compressing the second sheet, the flow port, and the first sheet together includes maximizing an area of contact between the first sheet and the portion of the elliptic body of the flow port and maximizing an area of contact between the second sheet and the another portion of the elliptic body of the flow port.

Method 500 may continue at step 508, which includes sealing the second sheet to the flow port and the first sheet includes first heating at least one of the second sheet, the flow port, or the first sheet, and then heat sealing the second sheet to the flow port and the first sheet. Method 500 may continue at step 510, which includes sealing the second sheet to the flow port and the first sheet.

In some aspects, method 500 may include other steps that can be performed in series or parallel with the described steps. For example, method 500 can also include manufacturing the flow port. In some aspects, manufacturing the flow port includes injecting a plastic into a negative mold of the flow port. Method 500 can also include installing one or more hoses to respective hose barbs of the flow ports installed in the biopharmaceutical liquid container. Method 500 can also include forming the biopharmaceutical fluid container from the sheets with a large opening at a bottom edge to accommodate the required number of biopharmaceutical flow ports inserted between the sheets, and then sealing the biopharmaceutical liquid container with the biopharmaceutical flow ports in the large opening.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:

1. A biopharmaceutical flow port comprising:
   a hose barb comprising a bore; and
   an elliptic body comprising a first end and a second end opposite the first end, the second end of the elliptical body coupled to the hose barb, the elliptic body comprising:
      an inlet on the first end of the elliptical body and an outlet on the second end of the elliptical body; and
      a flow passage that extends from the inlet to the outlet, the outlet fluidly coupled to the bore, the flow passage at least partially defined by:
         a first flow passage portion comprising a first cross-section, the first flow passage portion extending a length of the elliptical body from the first end to the second end; and
         a second flow passage portion coupled to the first flow passage portion, the second flow passage portion comprising a second cross-section different than the first cross-section, the second flow passage portion superimposed on the first flow passage portion and extending the length of the elliptical body from the first end to the second end, the flow passage configured to pass fluid through the elliptical body from the inlet through both the first flow passage portion and the second flow passage portion to the outlet of the flow passage;
      a first edge that extends from the elliptic body away from the flow passage in a first direction; and
      a second edge that extends from the elliptic body away from the flow passage in a second direction opposite the first direction.

2. The biopharmaceutical flow port of claim 1, wherein the hose barb is integrally formed with the elliptic body.

3. The biopharmaceutical flow port of claim 1, wherein the hose barb comprises a ridge configured to secure a conduit into fluid communication with the bore.

4. The biopharmaceutical flow port of claim 1, wherein the flow passage is defined at least partially by:
   the first cross-section of the first flow passage portion comprising an elliptical cross-section; and
   the first cross-section of the second flow passage portion comprising a circular cross-section.

5. The biopharmaceutical flow port of claim 4, wherein the first flow passage portion and the second flow passage portion are fluidly coupled.

6. The biopharmaceutical flow port of claim 4, wherein a radial centerline of the bore coincides with a radial centerline of the second flow passage portion.

7. The biopharmaceutical flow port of claim 4, wherein the second flow passage portion meets the bore at a rounded shoulder of an inner surface of the elliptic body defined by the flow passage.

8. The biopharmaceutical flow port of claim 7, wherein the flow passage comprises a frusto-conical inner surface portion of the elliptic body, the frusto-conical inner surface portion comprising a transition from the flow passage to the bore.

9. The biopharmaceutical flow port of claim 1, wherein the first flow passage portion is concentric within the second flow passage portion.

10. The biopharmaceutical flow port of claim 1, wherein:
   a diameter of the circular cross-section and a diameter of the bore are substantially equal,
   a radial centerline of the bore coincides with a radial centerline of the flow passage, and
   the flow passage meets the bore at a rounded shoulder of an inner surface of the elliptic body defined by the flow passage.

11. The biopharmaceutical flow port of claim 10, wherein the flow passage comprises a frusto-conical inner surface portion of the elliptic body, the frusto-conical inner surface portion comprising a transition from the flow passage to the bore.

12. The biopharmaceutical flow port of claim 1,
   the first cross-section of the first flow passage portion comprises a rounded rectangular cross-section; and
   the first cross-section of the second flow passage portion comprises a circular cross-section.

13. The biopharmaceutical flow port of claim 12, wherein the first flow passage portion and the second flow passage portion are fluidly coupled.

14. The biopharmaceutical flow port of claim 13, wherein a radial centerline of the bore coincides with a radial centerline of the second flow passage portion.

15. The biopharmaceutical flow port of claim 13, wherein the second flow passage portion meets the bore at a rounded shoulder of an inner surface of the elliptic body defined by the flow passage.

16. The biopharmaceutical flow port of claim 15, wherein a major dimension and a minor dimension of the rounded rectangular cross-section decrease from a first end of the elliptic body to a second end of the elliptic body, the second end of the elliptic body closer to the hose barb than the first end.

17. The biopharmaceutical flow port of claim 16, wherein an inner surface of the elliptic body comprises a transition from the flow passage to the bore.

18. The biopharmaceutical flow port of claim 12, wherein:
the bore and the second flow passage portion comprise a contiguous opening,
the second flow passage portion extends through the first flow passage portion into the hose barb, and
the circular cross-section extends outside the rounded rectangular cross-section.

19. The biopharmaceutical flow port of claim 1, further comprising a ribbed portion formed on an outer surface of the elliptic body, and the ribbed portion extends across the outer surface of the elliptic body from each of the first and second edges toward the hose barb.

20. The biopharmaceutical flow port of claim 1, wherein the first edge and the second edge are integrally formed with the elliptic body, and each of the first and second edges comprises a first curved surface and a second curved surface that mirrors the first curved surface and meets the first curved surface at an edge.

21. The biopharmaceutical flow port of claim 1, wherein the bore is defined by a first radial dimension at a first end near the elliptic body and a second radial dimension larger than the first radial dimension at a second end opposite the first end.

22. The biopharmaceutical flow port of claim 1, further comprising tabs that extend from the elliptic body.

23. The biopharmaceutical flow port of claim 1, wherein the first flow passage portion and the second flow passage portion are of substantially equal length.

* * * * *